United States Patent [19]

Hernandez et al.

[11] Patent Number: 4,931,949
[45] Date of Patent: Jun. 5, 1990

[54] METHOD AND APPARATUS FOR DETECTING GEAR DEFECTS

[75] Inventors: Walter C. Hernandez, Potomac; Edward A. Page, Kensington; Kenneth A. Lefler, Catonsville, all of Md.

[73] Assignee: Monitoring Technology Corporation, Falls Church, Va.

[21] Appl. No.: 171,853

[22] Filed: Mar. 21, 1988

[51] Int. Cl.⁵ .................. G06F 15/20; G01M 7/00; G01M 13/00

[52] U.S. Cl. .................... 364/497; 364/508; 364/474.17; 73/593; 73/607; 73/162; 73/660; 340/683

[58] Field of Search .............. 364/507, 508, 576, 581, 364/474.17; 73/862.06, DIG. 1, 660, 670, 577, 593, 602, 162; 340/683

[56] References Cited

U.S. PATENT DOCUMENTS

| | | | |
|---|---|---|---|
| 2,965,971 | 12/1960 | Pomernacki | 73/593 |
| 4,237,454 | 12/1980 | Meyer | 340/683 |
| 4,252,023 | 2/1981 | Pomernacki | 73/593 |
| 4,707,688 | 11/1987 | Thomas | 340/683 |
| 4,730,484 | 3/1988 | Olschefski | 73/660 |
| 4,758,964 | 7/1988 | Bittner et al. | 340/683 |

FOREIGN PATENT DOCUMENTS

| | | | |
|---|---|---|---|
| 0019414 | 2/1981 | Japan | 73/162 |
| 0934285 | 6/1982 | U.S.S.R. | 73/162 |

OTHER PUBLICATIONS

McFadden; "Low Frequency Vibration Generated by Gear Tooth Impacts"; NDT International, vol. 18, No. 5; Oct. 1985.

Primary Examiner—Parshotam S. Lall
Assistant Examiner—Ellis B. Ramirez
Attorney, Agent, or Firm—Mathews, Woodbridge & Collins

[57] ABSTRACT

A gear defect analyzing system records the interaction of each tooth of a gear system until the interaction begins to repeat and then processes the information in such a way as to identify defective gear tooth. Signals from a gear box are detected by an accelerometer and a shaft encoder and fed to an interface circuit and then to an analog signal preprocessing circuit. The preprocessing circuit conditions the signal so that it can be analyzed by a microcomputer. The system has the capability of identifying the class of incoming signals, determining the optimal time domain average, eliminating unwanted spectral components and interference, computing specific measurements relating to gear wear and then performing analysis of time history within a given system operating state to determine which gears and gear teeth are defective. By recording each tooth-to-tooth interaction over a period of time, and then processing the recorded matrix of data, it is possible to locate individual tooth defects. The system is also capable of detecting, classifying, and analyzing other types of hard-to-find defects.

11 Claims, 21 Drawing Sheets

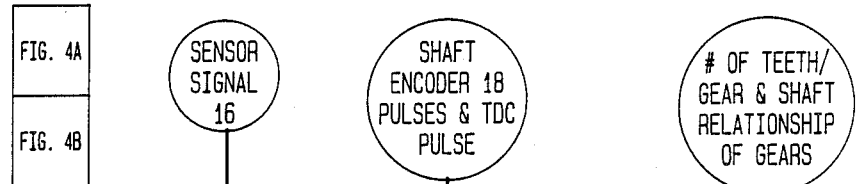

FIG. 4

| FIG. 4A |
|---|
| FIG. 4B |

FIG. 4A (SENSOR SIGNAL 16)

(SHAFT ENCODER 18 PULSES & TDC PULSE)

(# OF TEETH/ GEAR & SHAFT RELATIONSHIP OF GEARS)

STEP #1A
BAND PASS FILTER & EXTRACT SIGNAL ENVELOPE (SEE FIG. 5A)

STEP #1B
PULSE RATE INTEGER MULTIPLY & DIVIDE (SEE FIG. 5B)

STEP #1C
COMPUTE # OF SAMPLES (TAKEN AT GIVEN SHAFT ANGLE INCREMENTS NOT TIME INCREMENTS) FOR TIME DOMAIN AVERAGES (SEE FIG. 6)

STEP #1D
| A/D | CLOCK | TRIGGER |

STEP #2
COMPUTE OPTIONAL TIME DOMAIN AVERAGE FOR SAMPLE INTERVALS CORRESPONDING TO
(1) 1 CYCLE OF THE OVERALL GEAR SYSTEM
(2) 1 CYCLE OF SELECTED SUBSYSTEMS OF GEARS
(3) 1 CYCLE OF A GIVEN SHAFT OF THE SYSTEM
(SEE FIG. 7, 13)

STEP #3
SYSTEM STATE CLASSIFICATION BASED ON SPECIFIED PROPERTIES OF THE SIGNALS, DIVIDES THE SYSTEM OPERATION INTO A # OF STATES FOR WHICH MEASURES OF GEAR CONDITIONS CAN BE COMPARED WITHIN A GIVEN STATE. LABEL EACH TIME DOMAIN AVERAGE WITH THIS STATE

STEP #4
IDENTIFICATION & ELIMINATION OF SPECTRAL COPMPONENTS (IN THE ABOVE VIBRATION TIME DOMAIN AVERAGES) INDUCED BY GEAR SYSTEM MODULATION EFFECTS (SEE FIG. 8A, 8B, 8C)

STEP #5
ELIMINATE INTERFERENCE IN THE ABOVE TIME DOMAIN AVERAGES INDUCED BY A DEFECT ON ANOTHER GEAR OR COMPONENT (SEE FIG'S. 9A, 9B, 9C)

STEP #6A
COMPUTE SPECIFIC MEASURES RELATING TO GEAR CONDDITION FROM THE OVERALL TIME DOMAIN VIBRATION AVERAGE. THESE MEASURES ARE SPECIFIC TO DIFFERENT DEFECTS SUCH AS CRACKS OR PITTING ALSO COMPUTE THE RESIDUAL NOISE IN THESE PATTERNS (SEE FIG. 10A)

STEP #6B
COMPUTE CONDITIONS MEASURE OF INDIVIDUAL GEAR TOOTH COMBINATION FROM THESE TIME DOMAIN AVERAGES (SEE FIG. 10C, 10D, 10E)

STEP #6C
AMPLITUDE OF MODULATION INDUCED SPECTRAL LINES

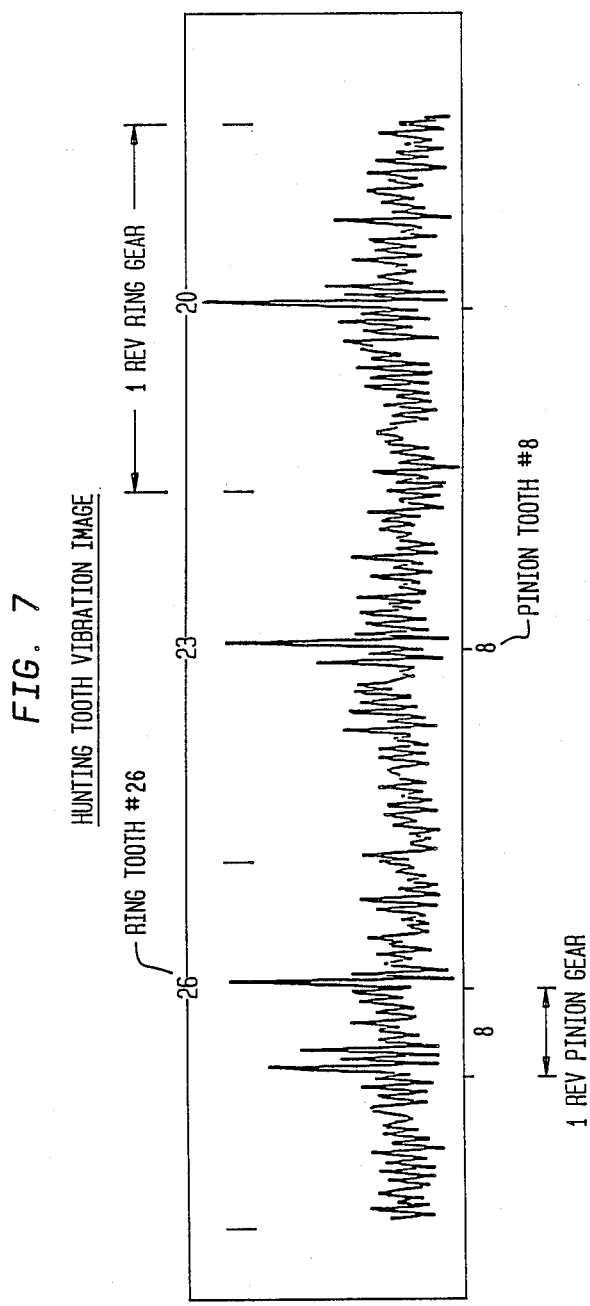

FIG. 8A
INDIVIDUAL GEAR MESH VIBRATION PATTERN
WITH STRONG INFLUENCE FROM SYSTEM MODULATION EFFECTS
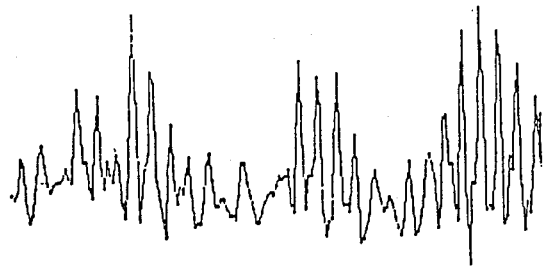
IDENTIFICATION & ELIMINATION OF
MODULATING INDUCED SIGNAL COMPONENTS
RESULTING GEAR MESH PATTERN
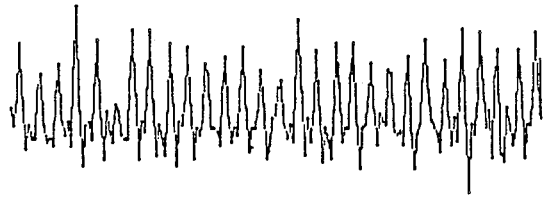

EXAMPLE GEAR IMAGE DFT

FIG. 9A
REMOVAL OF GEAR DEFECT SIGNATURE
CONTAMINATION FROM ADJACENT GEAR
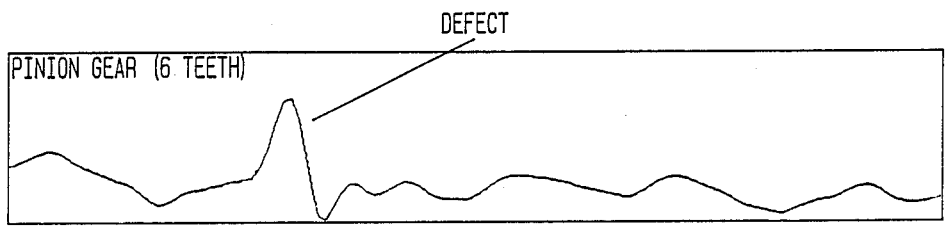
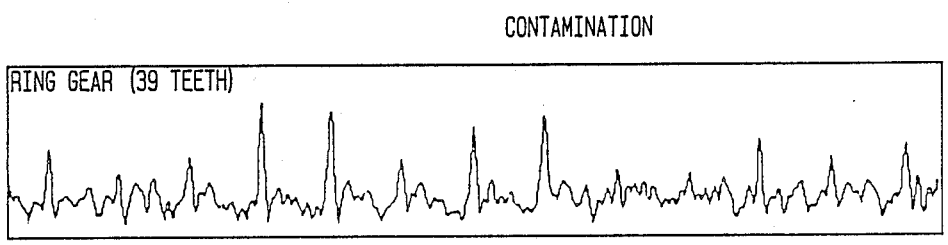
CONTAMINATION
REMOVAL
PROCEDURE
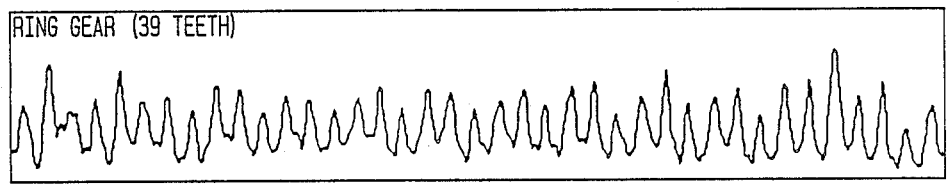

GENERALIZED GEAR PATTERN
DECONTAMINATION PROCESS

PEAK RESIDUAL FEATURE

NON-MESH ENERGY RATIO FEATURE

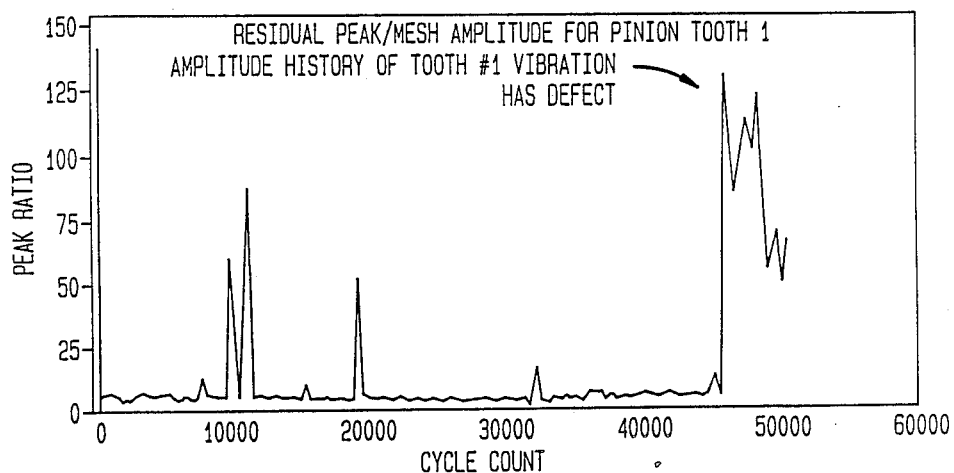
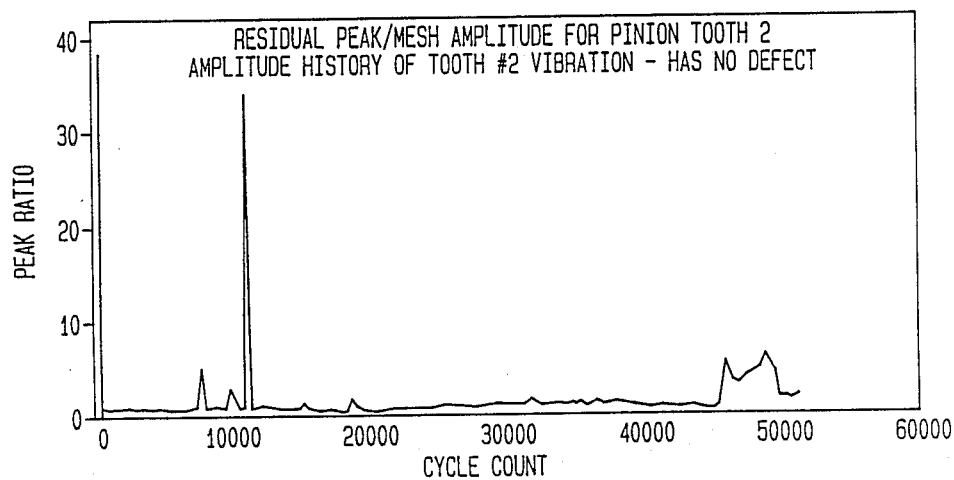

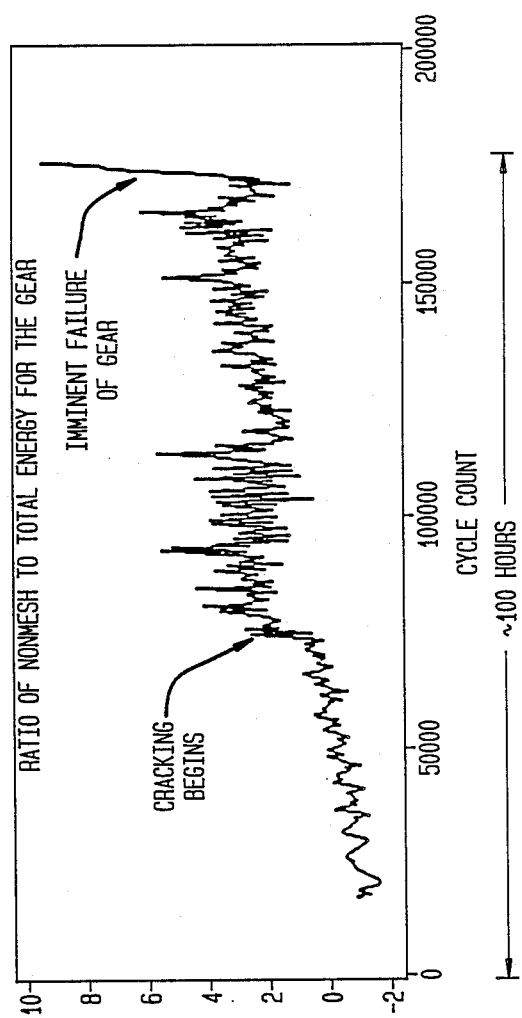

TOOTH DEFECT

← HT$_{AB}$ →

← HT$_{CD}$ →

DEFECT          DEFECT ENVELOPE

← HT$_{ABCD}$ →

← ENVELOPE OF DEFECT OVER HT$_{ABCD}$ →

METHOD AND APPARATUS FOR DETECTING GEAR DEFECTS

BACKGROUND OF THE INVENTION

1. Field of the Invention

This invention relates to a method and apparatus for detecting and analyzing gear defects.

2. Related Art

Several attempts are disclosed in the prior art literature to analyze vibrational systems. Many of those attempts are highly complex and limited in their capability.

U.S. Pat. No. 4,520,674 entitled VIBRATION MONITORING DEVICE is typical of recent prior art systems. A signal generated by a vibration monitor is initially processed by a signal conditions module which includes anti-aliasing filters to enhance the accuracy of the data collected. Further preprocessing is performed by a multi-function module which also increases the speed and reliability of the system. The data is subsequently analyzed by a microprocessor and displayed if desired on a monitor.

U.S. Reissue Pat. No. RE 31,750 entitled DATA ACQUISITION SYSTEM is similar to the foregoing concept. Signal information is brought into a multi-channel multiplexer. Signal pick up is performed by self-amplified accelerometers. The system subsequently performs trend analysis on the historical data which consists of representative amplitudes of stored electrical signals.

U.S. Pat. No. 4,429,568 entitled ACOUSTICAL DEFECT DETECTION SYSTEM describes an invention in which the incoming signal is also preconditioned. The preconditioning is performed through the use of amplifiers, a high pass filter, a low pass filter, a full wave rectifier and an analog/digital converter.

U.S. Pat. No. 4,574,633 describes APPARATUS FOR DETECTING TOOL DAMAGE IN AUTOMATICALLY CONTROLLED MACHINE TOOLS wherein historical data is compared to present data.

The following prior art patent references describe possibly relevant systems for detecting the deterioration of gears. U.S. Pat. Nos. 3,758,758; 3,842,663; 4,335,612; 4,550,603 and 4,550,604. Certain of the foregoing patents relate to specific types of gears. For example, U.S. Pat. No. 3,758,758 relates specifically to the meshing of helicopter gears and U.S. Pat. No. 4,335,642 relates to a method of detecting irregularities on beveled gears. U.S. Pat. Nos. 4,550,603 and 4,550,604 both relate to gear inspection techniques.

Lastly, the prior art patent literature describes other systems of lesser relevance. For example, U.S. Pat. No. 4,352,293 includes a detailed description of Fourier analysis. U.S. Pat. No. 3,913,084 includes a discussion of the use of accelerometers in the context of noise detectors and analyzers. U.S. Pat. No. 3,694,637 describes a relatively simple system for analyzing wear on a tool in which a minicomputer is used for the purpose of analyzing the ultimate results.

A common method for performing vibration (or acoustic, torque, or force) based analysis of operating gear systems involves use of spectrum or cepstrum analysis instrumentation. This instrumentation allows amplitude estimation of vibrations related directly to gear tooth meshing frequencies. These amplitudes are then compared over time or between like machines, and conclusions on gear status are reached. Such methods give overall measures of gear performance and are not very sensitive to defects localized on the gear, and are subject to background interference. In addition, observations over time, or comparisons between similar machines is required to interpret these measures. The present invention describes a method for obtaining more detailed gear condition information on a tooth-by-tooth basis, and allows comparison among the teeth for interpretation. Disclosed are methods to extract the tooth-by-tooth information in the presence of numerous forms of interference, and to allow construction of a gear diagnostic image for further examination.

Another approach, explored specifically in the helicopters preventive maintenance industry, involves time domain averaging of vibration signals and computing statistical measures such as the fourth and sixth moment, from these time domain averages. Changes in these measure over time is the basis of the approach. This technique does not produce a tooth-by-tooth level of analysis and is subject to interference, thereby limiting its sensitivity and reliability in such applications.

Insofar as understood, none of the prior art taken individually or in combination teach or suggest the present invention which includes, among other things, the capability of analyzing tooth-to-tooth interactions over a long period of time, and then stacking the interactions in such a way as to make a gear defect detectable.

SUMMARY OF THE INVENTION

Briefly described, the invention comprises a method and apparatus for performing advanced vibration analysis. Signals from an accelerometer and a shaft encoder are fed through an interface circuit to an analog signal preprocessor prior to being fed into a microcomputer. The analog signal preprocessor typically passes the signal through full wave rectifiers and low pass filters to demodulate the signal in order to extract the amplitude envelope. The envelope is then supplied as an input to an analog/digital converter so that the signal can be processed by the microcomputer. The signal may also be conditioned in other manners depending upon the nature of the phenomenon being investigated. The digitized signal is then classified by the system based upon specific properties of the signal and the signal is processed to compute the optimal time domain average. Thereafter, the signal is further processed by the computer to identify and eliminate spectral components and to eliminate interference after which computations are made to measure gear wear and detect gear defects. Time history analysis is performed within a given system operating state and alarm logic is used to alert the system user if there are significant changes in status. Ultimately the results are presented in the form of a status report, a monitor display and/or an automated alarm or shut down reaction.

One important advantage of the system is its ability to employ hunting tooth vibration pattern analysis to analyze the intermeshing reaction of two or more gears. Each tooth-to-tooth interaction is recorded until the pattern begins to repeat. Subsequent recordings are averaged with respect to previous records to produce a unique pattern to identify which tooth-to-tooth interaction is likely to involve defective teeth. Subsequent analysis makes it possible to detect which of the teeth in the tooth-to-tooth interaction is likely to be the defective tooth.

These and other features of the inventions will be more fully understood by reference to the following drawings.

BRIEF DESCRIPTION OF THE DRAWINGS

FIGS. 4 and 4A-B are flow charts describing the steps by which the system analyzes signals and detects gear defects.

FIG. 7 is a graph of the vibration image produced over a hunting tooth cycle for a single pair of meshing ears.

FIG. 8A illustrates the effect of eliminating modulation induced signal components from a gear vibration pattern.

FIG. 9A illustrates the effect of the removal of gear defect signature contamination from an adjacent gear.

FIG. 10D illustrates the amplitude history of an individual defective tooth over a period of time.

FIG. 10E illustrates the amplitude history of a nondefective individual tooth over a period of time.

FIG. 11 illustrates a history of a gear over approximately 100 hours from the initiation of cracking to the imminent failure of the gear.

DETAILED DESCRIPTION OF THE INVENTION

During the course of this description like numbers will be used to identify like elements according to the different figures which illustrate the invention.

Figure 1:
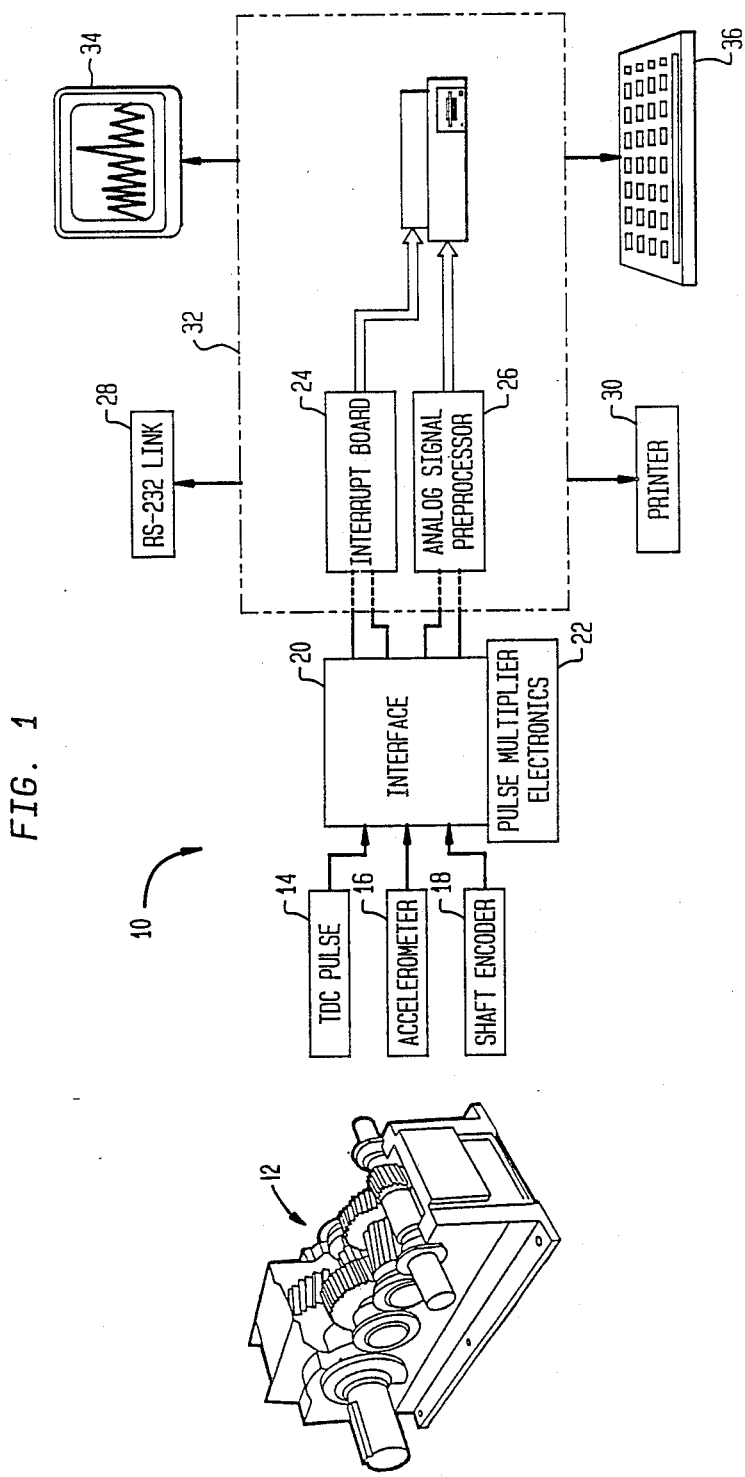
FIG. 1 is a block diagram of the preferred embodiment of the present invention.

The basic invention 10 according to the preferred embodiment is illustrated in FIG. 1. A gear system 12 produced a Top-Dead-Center (TDC) pulse 14 as well as inputs from accelerometer 16 and shaft encoder 18 to interface 20. Pulse multiplier electronics 22 can be used to speed up, i.e. multiply the frequency of the pulses so that they can be processed by microcomputer 32. The outputs of interface 20 provide inputs to intercept board 24 and analog signal preprocessor board 26 which are preferably housed within the chassis of microcomputer 32. Microcomputer 32 preferably comprised an IBM-PC/AT 80286 type of microprocessor which has connections to peripherals such as an RS-232 communications link 28, a printer 30, a high resolution color monitor 34 and keyboard 36.

Interrupt board 24 is a commercially available device that serves the purpose of notifying the microcomputer 32 that another TDC pulse has arrived so that the microcomputer 32 can count the number of encoder pulses to the next TDC pulse.

Figure 2A:
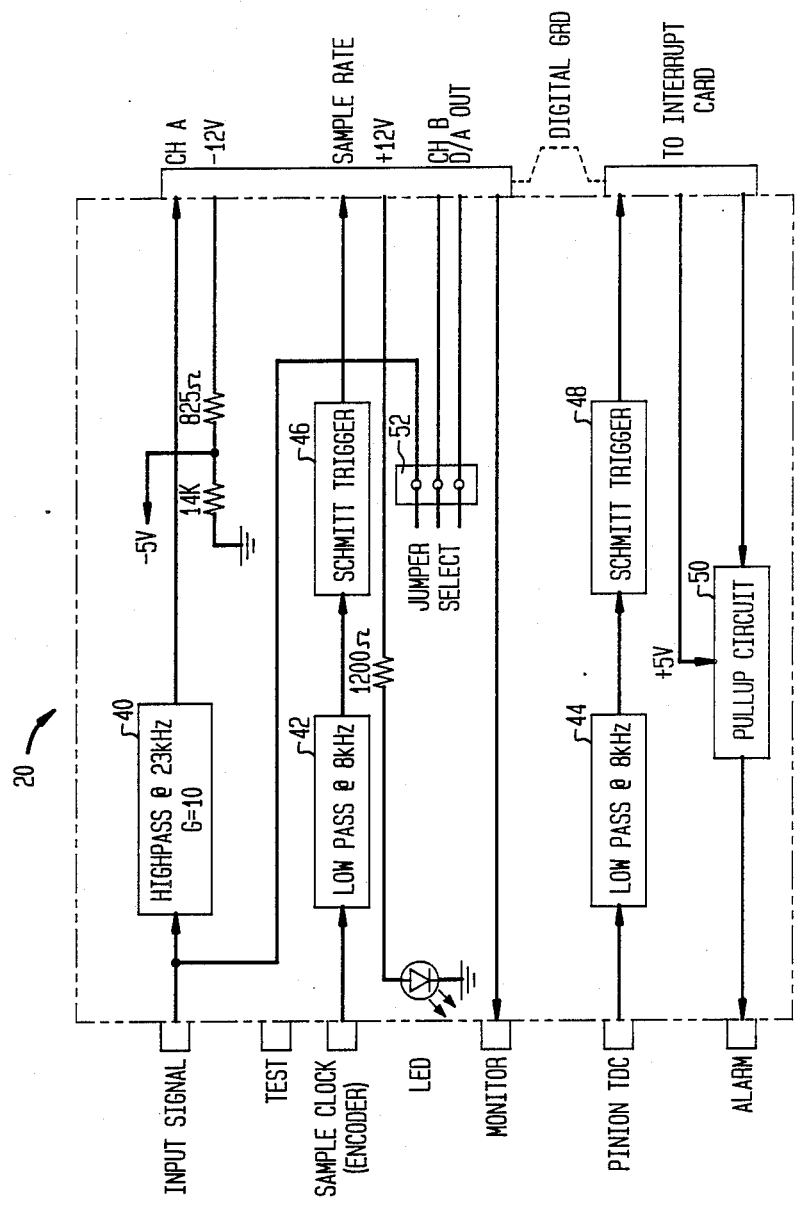
FIG. 2A is a block schematic diagram of the interface circuit illustrate din FIG. 1.

Inteface 20 is illustrated in detail in FIG. 2A. The input signal from accelerometer 16 passes through a high pass filter 40 as channel A to the analog signal preprocessor 26. The output from the shaft encoder 18 provides the input to low pass deglitching filter 42 and Schmitt trigger 46 and from there to analog preprocessor board 26. Likewise, the pinion TDC signal input pulse 14 is stripped of its high frequency characteristic by a low pass filter 44 and shaped by a Schmitt trigger 48 and passed from there to the interrupt board 24. If the system 10 signals an imminent failure, a pulse is applied to pull up circuit 50 which sounds an alarm. Jumper select switch 52 permits the user of the system 10 to route the raw accelerometer signal 16 to channel B of the analog preprocessor board 26, or to input a test signal generated by the D/A output on the analog board 16.

Figure 2B:
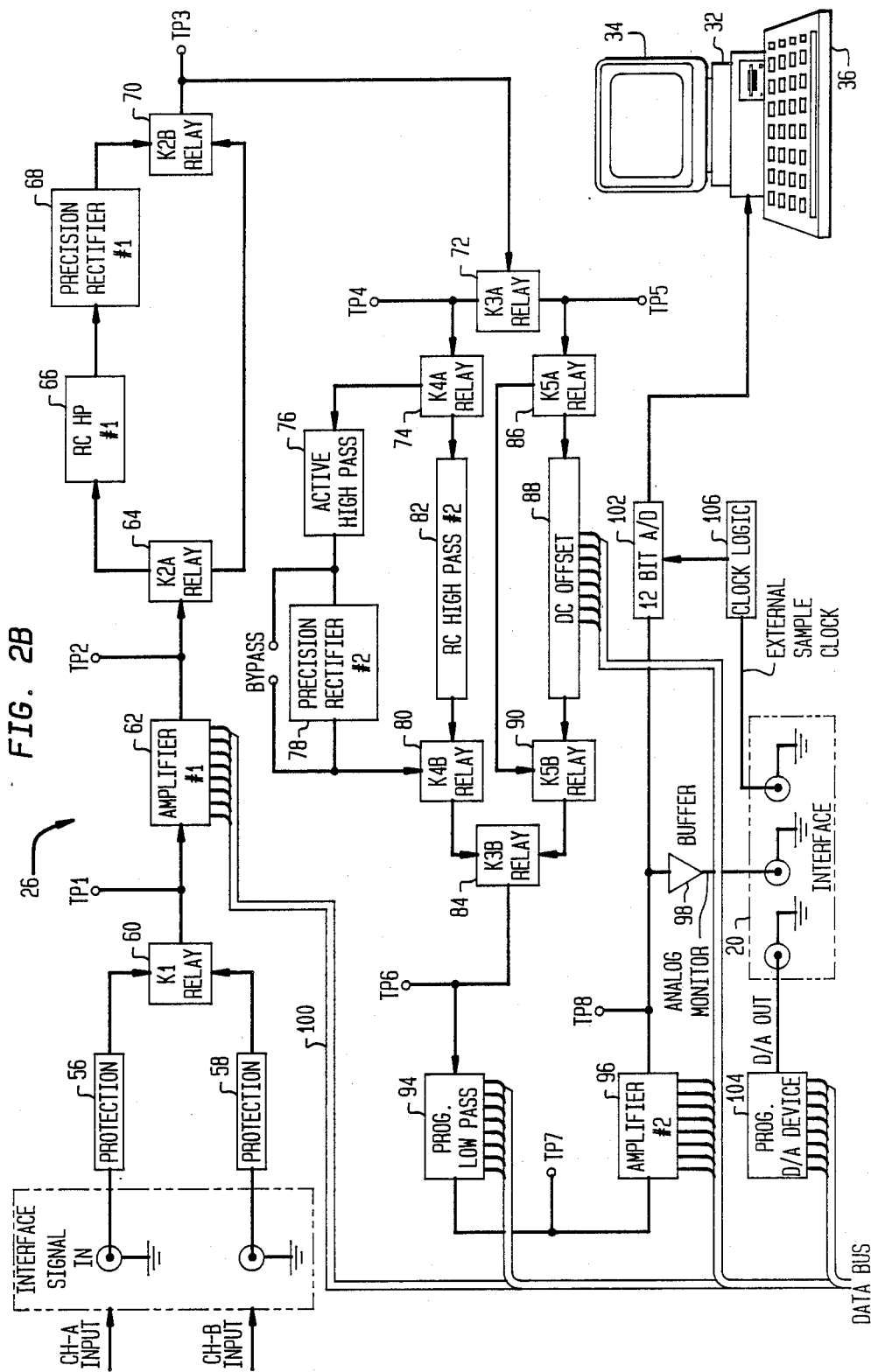
FIG. 2B is a block schematic diagram of the analog signal preprocessor circuit illustrated in FIG. 1.

The analog signal preprocessor circuit 26 is illustrated in detail in FIG. 2B. The incoming analog signal from the interface circuit 20 input on channel A first passes through a protection device 56 and relay 60 before it is amplified by the first amplifier 62. A second relay 64 typically steers the signal through an RC high pass filter 66 and a precision rectifier 68 which outputs the signal through another relay 70. High pass RC filter 66 compensates for low frequency DC drift and the first precision rectifier circuit 68 provides for full wave rectification. In a minority of circumstances the relays 64 and 70 may be set to bypass the RC filter 66 and rectifier 68, especially in those situations where low frequency drift is not a problem or high frequency filtering might remove useful information.

The output from relay 70 provides the input to relay 72 which has the option of steering the signal to either relay 74 or relay 86, both of which in turn have the option of steering the signal to two separate directions respectively. Under most circumstances, the signal will be directed through DC offset 88 to relay 90 and then to relay 84. Alternatively, relay 86 could bypass DC offset 88 and route the signal directly to relay 90. It is also possible for input relay 72 to route the signal to relay 74 where the signal could be directed either through RD-high pass 82 or active high pass 76 and precision rectifier 78. Relay 80 can then pass either of these signals to relay 84.

Relay 84 passes its output signal through programmable low pass filter 94 and a second amplifier 96 as an input to a 12 bit analog/digital converter 102. An external sample clock input from interface 20 is processed by clock logic 106 and forms a second input to the 12 bit analog/digital converter 102. Analog/digital converter 102 converts the analog input from amplifier 96 to a digital form suitable for processing by microcomputer 32. Data bus 100 programs the positions of Relays 60, 64, 70, 72, 74, 80, 84, 86 and 90; the gain of amplifier 62, the voltage offset of DC offset circuit 88, the cutoff frequency of low pass filter 94, the gain of amplifier 96, and programs the digital-to-analog converter device 104 whose output can be jumpered through interface box 20. The analog signal preprocessing circuit 26 also includes 8 test points TP1 through TP8 for the purpose of signal monitoring. The setting of relays 60, 64, 70, 72, 74, 80, 84, 86, and 90 depends upon the conditioning that is required of the input signal prior to processing by the microcomputer 32. This in turn depends upon the characteristics of the input signal and the nature of the system being monitored, for example, it could be gears, it could be roller bearings, it could be a journal bearing, etc.

Baseboard processing of accelerometer signal 16 is identical to the above discussion except that relay 60 is switched to accept the output of protection device 58 which limits accelerometer signal 16 on channel B input.

Figure 3:
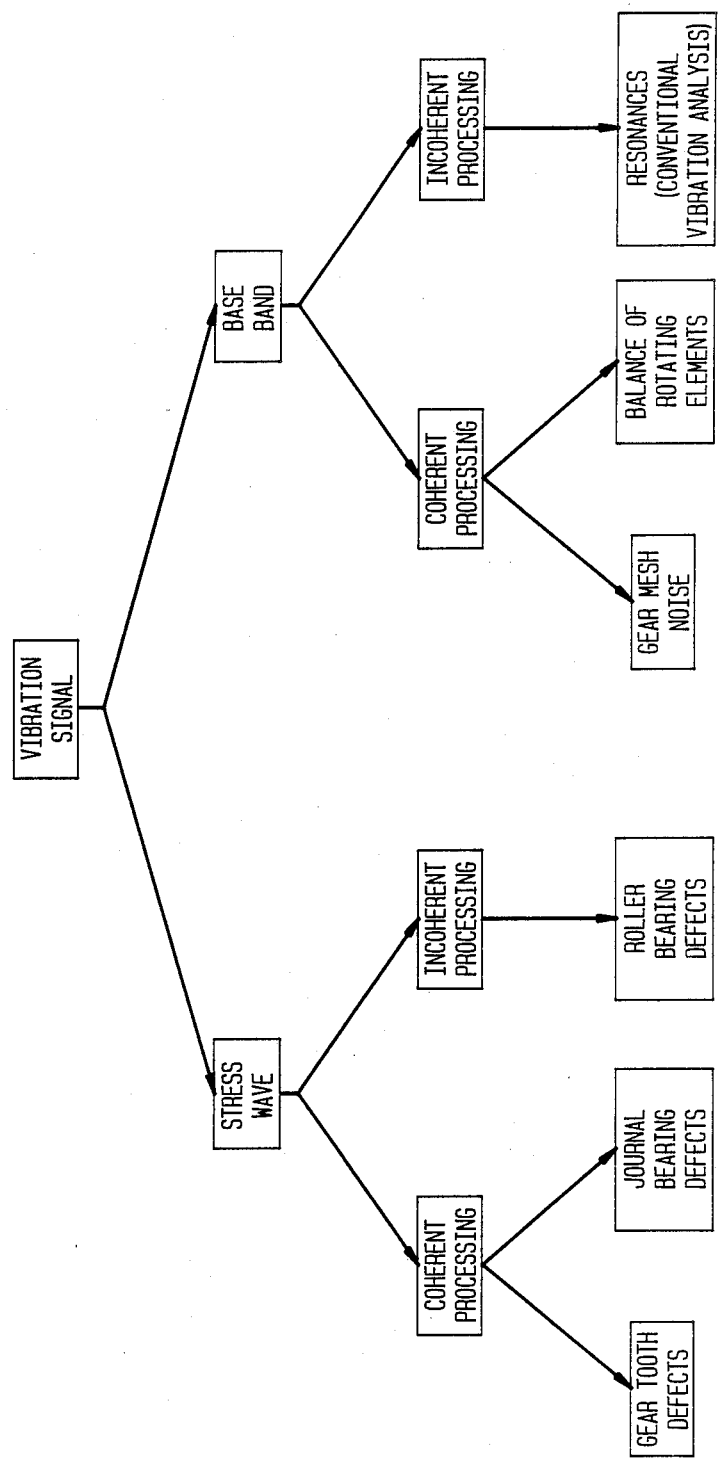
FIG. 3 is a chart describing the optimum processing steps for analyzing various different types of mechanical vibrations.

Gear defect analysis according to the present invention involves processing vibration signals in a variety of ways to optimize detection of specific defects. FIG. 3 illustrates that the detection of gear defects such as cracks and pitting involves coherent processing of stress wave signals, whereas, for example, monitoring for gear mesh noise or balance would preferably rely upon band pass vibration information.

Figure 4B:
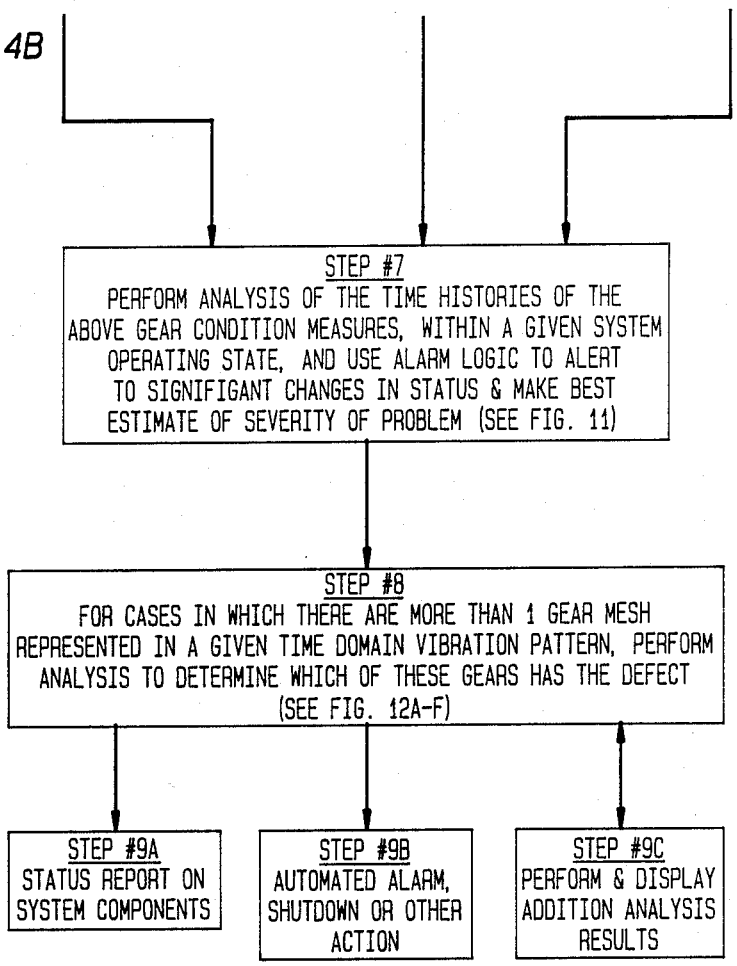

FIG. 4A-B illustrates the steps in the preferred method employed to detect and analyze incoming signals. These are steps that are performed by the elements described in FIGS. 1, 2A, and 2B.

Figure 5A:
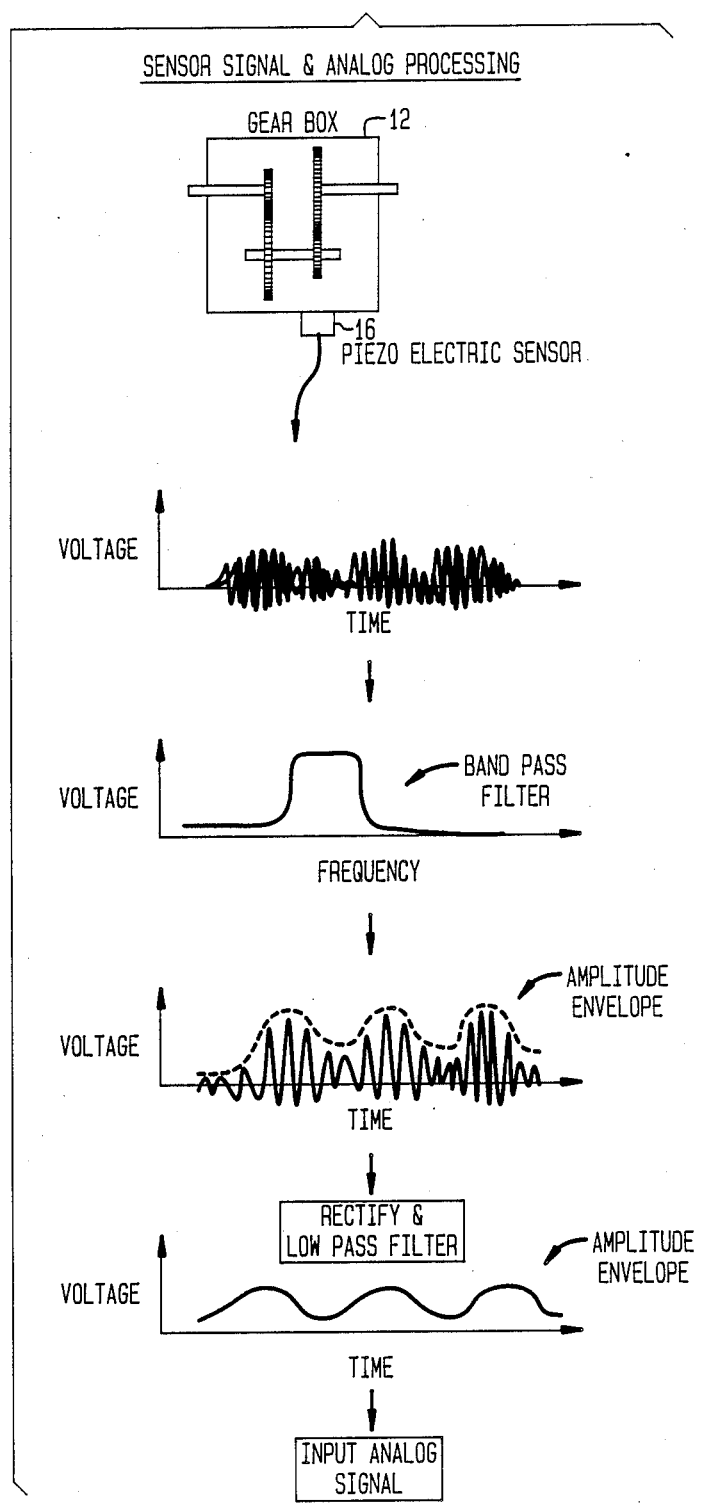
FIG. 5A illustrates the steps by which analog sensor signals are processed.

The first step in the preferred method illustrated in FIG. 4A-B comprises the detection and conditioning of the sensor signals. As shown in FIG. 5A, an off-the-shelf sensor 16 (typically a piezoelectric vibration sensor or acoustic microphone sensor) mounted on or near the gear assembly 12 to be monitored, would provide the input signal to the gear defect analyzer system 10. Piezoelectric sensors 16 are often selected to have a resonant frequency in the 20-60 KHz range and therefore, band pass filters such as high pass filter 40 in interface circuit 20 are used to pass frequencies centered on those resonant frequencies. The system 10 is capable of automatically alternating between two frequency bands (e.g. base band and 40 KHz band) thereby providing additional diagnostic information as well as providing information allowing for the classification of the operating state (e.g. RPM and load) of the gear assembly 12. The method for this is discussed in further detail with reference to FIG. 6 et seq. The incoming signal is then passed through electronic full wave rectifiers, such as precision rectifier 68 illustrated in FIG. 2B and then through low pass filters such as filter 94 to demodulate the signal in order to extract its amplitude envelope, which is the signal input to the analog/digital converter 102. The progression of the signal from the piezoelectric sensor 16 to the analog-to-digital converter 102 is illustrated schematically in FIG. 5A.

Figure 5B:
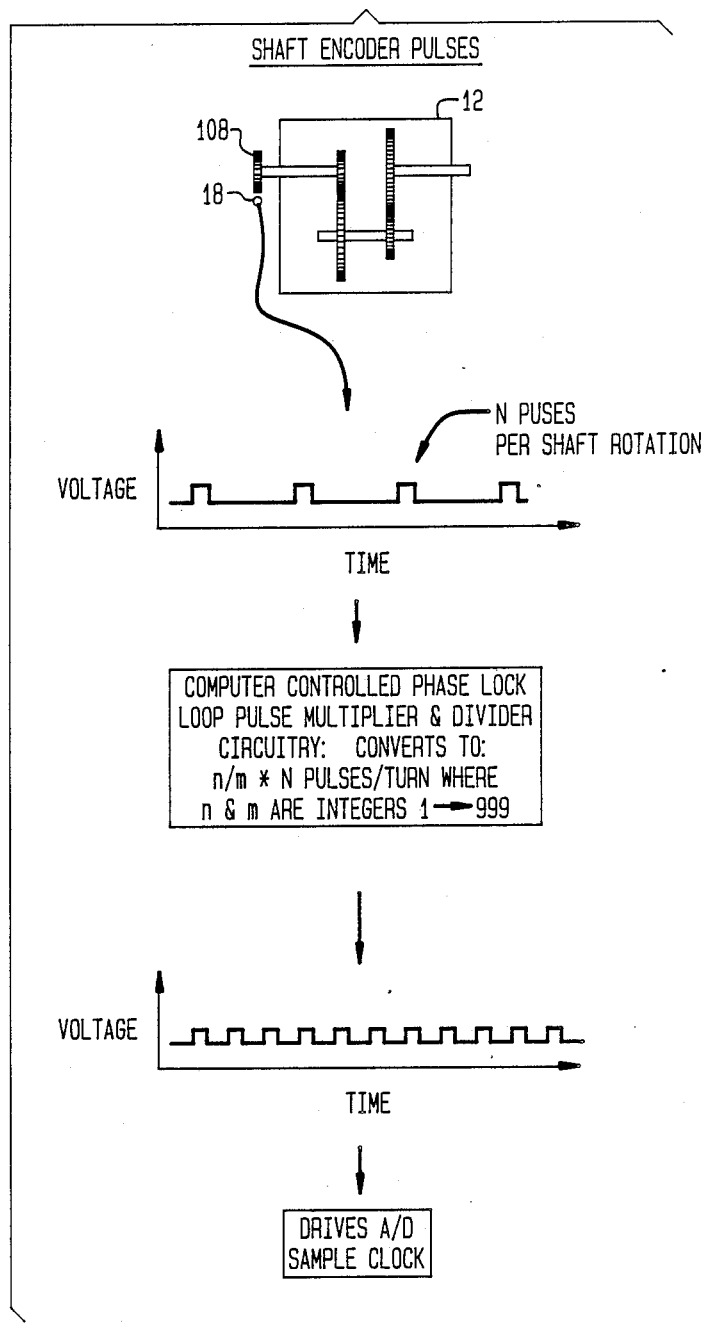
FIG. 5B illustrates the steps by which the shaft encoder pulses are detected.

The shaft position encoder 18 can consist of a mounted gear or reflecting surface such that a magnetic pick up 18 or optical pick up produces a pulse for each angular increment of shaft rotation. For example, as shown in FIG. 5B, a gear with 120 teeth would produce a pulse every 3 degrees. The number of pulses/turns often needs to be adjusted for proper gear mesh monitoring. For example, 120 teeth could be adjusted to produce 160 pulses ($4/3 \times 120 = 160$). For this a pulse multiplier/divider phase lock loop circuit 22, as shown in FIG. 1, is used with the multiplier/divider integer ratio computer control. A lock signal from the circuit 22 is also computer monitored to insure that this output pulse rate is locked to shaft angle. As a second check on the encoder pulses, a top dead center pulse is often used so that the computer 32 can check that it has received the proper number of samples/shaft turn pulses. A TDC pulse (Top-Dead-Center pulse) is a once per shaft revolution pulse whereas encoder pulses are multiple pulses per shaft revolution. The TDC is needed for:

a. a check that an encoder pulse was not missed. This is important to the method. For example, computer 32 would verify that the proper number of encoder pulses arrived for each TDC pulse.
 b. relating the vibration tooth images to a specific teeth on the gear.
 c. to allow the test to be restarted and still have the tooth images line up.
 d. in general, a TDC pulse is used for both the input and output shaft, allowing restarts to keep alignment on the overall tooth-by-tooth time domain average.

The TDC pulse preferably comes from a reflecting surface attached to the shaft such that light reflecting off the surface produces one pulse per shaft revolution. FIG. 5B illustrates the steps employed by the system to produce digital sample clock pulses from the shaft encoder mechanism 18.

Figure 6:
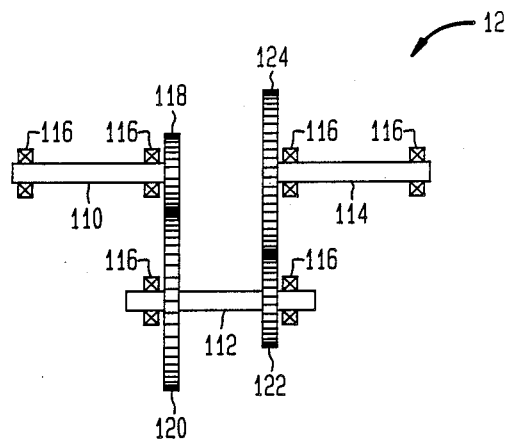
FIG. 6 illustrates a typical four gear/three shaft reverted gear train.

The gear analyzer system 10 requires input parameters identifying the number of teeth of each mating pair of gears and the ratio of their shaft rotations to the shaft containing the shaft encoder 10. With this information, the computer 32 can then determine the number of shaft encoder pulses and fractions thereof for time domain averaging over one cycle of the overall system, or one cycle of selected gear subsystems and/or one cycle of a given shaft. This data represents the key parameters required for performing shaft coherent time domain averaging necessary to proceed to the next step. A stylized gear train is illustrated in FIG. 6 and is similar to the CRT display that elicits the initial input parameter with regard to the number of gear teeth and their relative ratios.

The sensor analog signal envelope illustrated at the bottom of FIG. 5A is digitized using an off-the-shelf 12 bit analog-to-digital converter 102 with a digital sampling clock 106 controlled by the encoder pulses from shaft encoder 18. The digital signal (e.g. base band and stress wave band selectable) is then processed according to the next step.

The second step of the method illustrated in FIG. 4A-B, is to take the digitized vibration data and optimally time domain average it over (1) one cycle of the overall gear system (2) one cycle of selected gear subsystems, and (3) one cycle of a given shaft of the system. Although computing the time domain average for the complete gear system 12 is the most precise approach, it may not be practical in some applications and the time domain average for pairs of the gears (e.g. hunting tooth pattern for a pair of gears) would serve as the next best approximation. FIG. 7 illustrates a hunting tooth vibration image which is time domain averaged for a single gear pair.

In performing the above computations, two features of the technique should be emphasized. Namely:

1. When the encoder 18 is not on one of the shafts of the gear system 12 to be time domain averaged, an algorithm (discussed below) which can average over non-integer sample lengths and not cumulate errors is used.

2. The time domain averaging is "optimally" averaged (or weighted) to take into account background noise level variations, RPM and load vibrations.

The advantages of using the hunting tooth vibration pattern analysis approach are discussed in more detail later on, but can be summarized as follows:

1. It allows detection of anomalous vibrations produced by individual pairs of meshing teeth (as shown in FIG. 7 - only when tooth number 8 of the pinion gear meshed with a limited set of teeth (in the vicinity of Ring teeth 20-26) on the mating gear did anomalous vibrations appear). This is only clearly observable using the foregoing hunting tooth vibration analysis approach.

2. By monitoring changes in vibration levels of individual pairs of teeth over time, an accurate estimate of the remaining interference due to background noise can be obtained. This is critical in order to identify significant changes in the pattern relating to identify defects.

3. Only through the use of the foregoing hunting tooth pattern and the fourth step of the method, described subsequently, can interference be removed from a given gear vibration pattern due to a defect on its mating gear.

4. Only through the use of the hunting tooth gear pattern can one of two gears on a given shaft, each of which mates with a different gear, be identified as having the specific defect. This technique involves detecting which hunting tooth pattern contains a modulation attributed to the gear defect meshing rate. See Step 8 described in further detail subsequently.

The third step in the method is to classify the system state. Based upon signal characteristics (e.g. the baseband spectrum mean, variance and/or shape) the operating state of a gear system (e.g. constancy and relative level of load and RPM) can be monitored such that measures of gear condition (computed from baseband or stress wave band) over time can be compared with a given operating state.

Such a procedure is required for machinery used under variable operating conditions so that changes in the time domain gear vibration pattern due to gear defects can be reliably distinguished from significant changes in gear meshing dynamics.

The foregoing procedures can be generalized for many other applications where specific characteristics of the sensor signal can define the operating state of a system so that other aspects of that signal can be analyzed for estimates of machine component condition status.

Figure 8B:
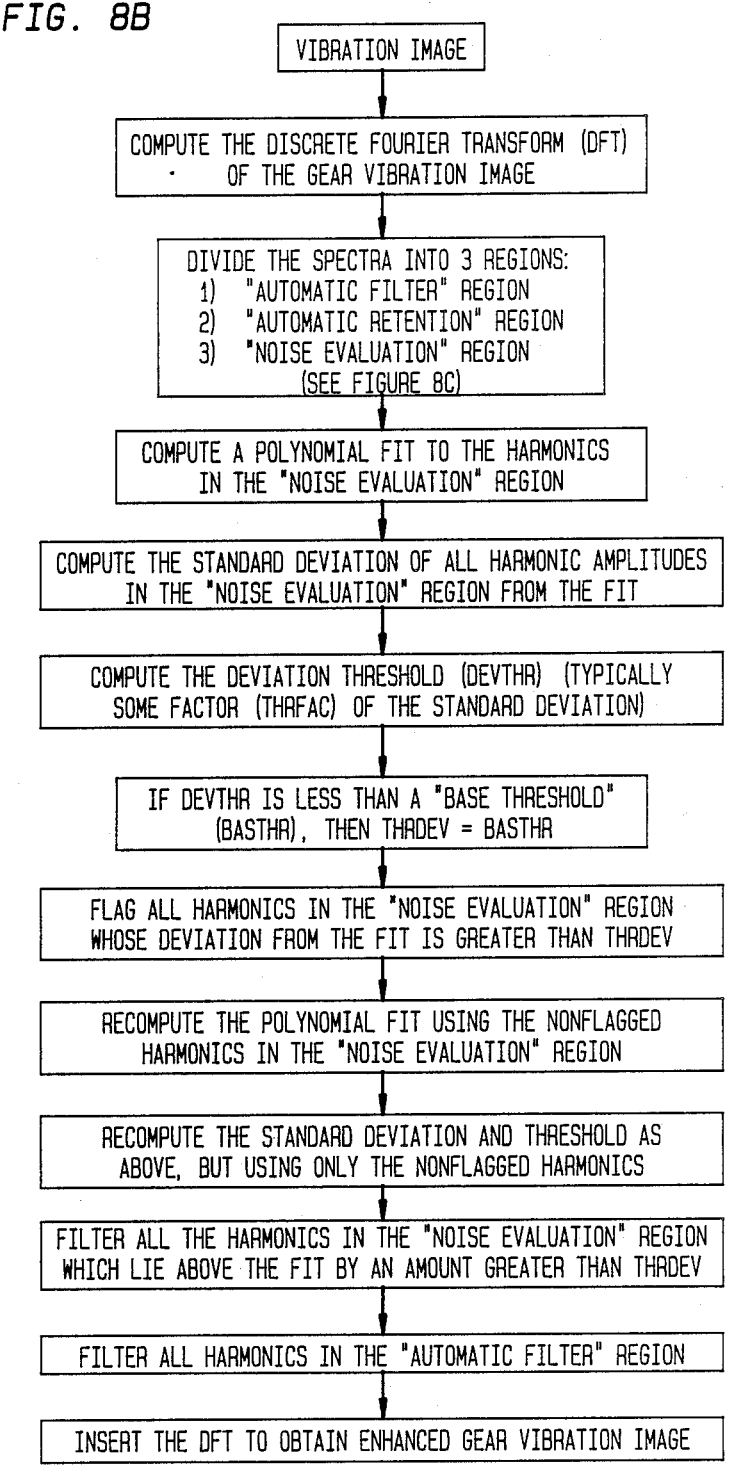
FIG. 8B represents an algorithm for removing interfering spectral components from a gear vibration image.
Figure 8C:
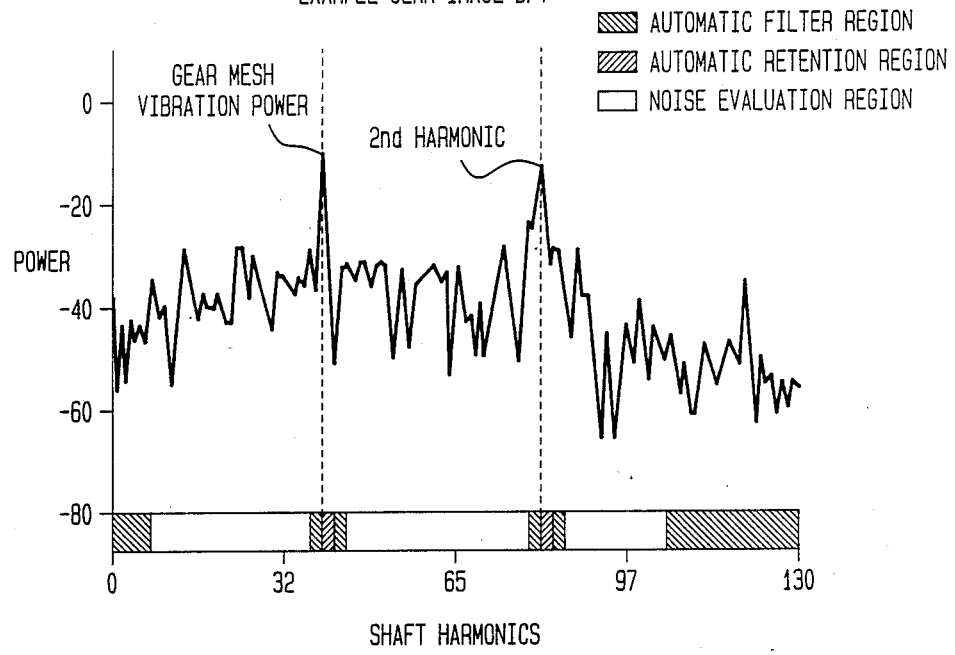
FIG. 8C illustrates an example of a Discrete Fourir Transform Vibration Image and shows the filtering regions involved in 8B.

The fourth step in the system as illustrated in FIG. 4A-B is the elimination of modulation interference. Shaft runout, gear pitch cycle runout, and other factors can cause gear mesh loading vibrations which can induce vibration amplitude and phase modulation that interferes with the time domain pattern computed in Step No. 2. It is therefore necessary to automatically identify the spectral components containing this interference and minimize their effect. The technique employed according to the present invention involves computing Discrete Fourier Transforms (not FFT's) of the vibration pattern, modeling the overall spectral background form, and then use detection criteria to identify undesirable characteristics of the spectrum, which are then filtered out. The amplitudes of those characteristics are stored for analysis for other system defects (e.g. U-joints, bearings, balance, etc.) relating to the same source of modulation. FIG. 8A illustrates an example of the effectiveness of this procedure, outlined in FIGS. 8B and 8C.

Figure 9B:
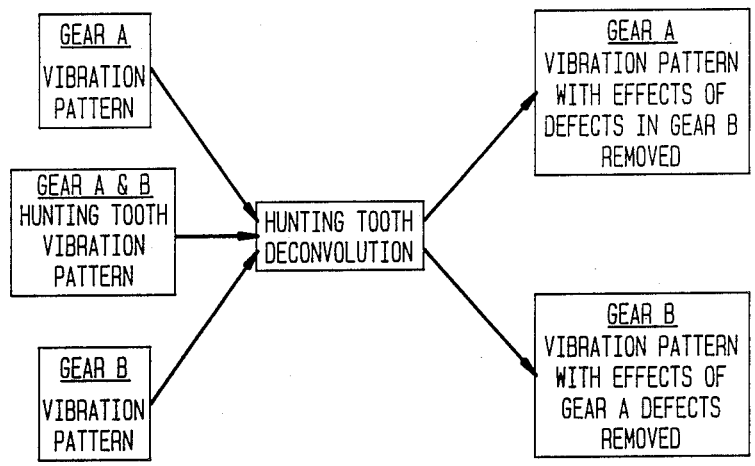
FIG. 9B describes the gear pattern decontamination process.
Figure 9C:
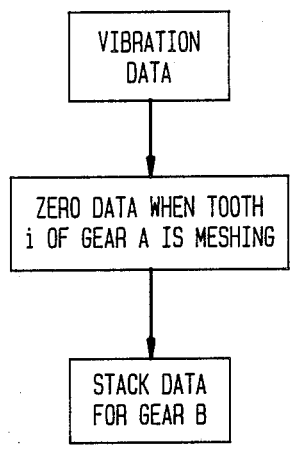
FIG. 9C represents an algorithm for removing the contribution of a defective tooth on a single gear from the gear vibration images of other gears.

Step No. 5 of the method illustrated in FIG. 4 A-b comprises a process for gear vibration pattern decontamination. A significant defect on one gear can induce interference on the vibration pattern of its mating gear, the magnitude which depends on the specific tooth ratios involved. FIG. 9A illustrates an example of such a decontamination process for removing the interference caused by a defect on a 9 tooth pinion gear from the vibration pattern of its mating 39 tooth ring gear. By eliminating, from the hunting tooth pattern, the contribution of those pairs of meshing teeth that only include the defective pinion tooth, the ring gear vibration pattern can then be computed with this interference removed. FIG. 9B illustrates the generalized schematic steps for this process outlined in FIG. 9C. Defects on tooth i of a gear A, which are apparent in the coherent stack for gear A, also tend to affect the coherent stack for other gears, e.g., gear B. The distorting or leakage effect of tooth i of gear A can be eliminated from the coherent stack of gear B by simply eliminating all data for tooth i of gear B before doing the stack for gear B. Linear processors such as spectral filtering, etc. would not be as effective since the vibration produced by the defective tooth is a highly non-linear function of which ring tooth it meshes with.

Figure 10A:
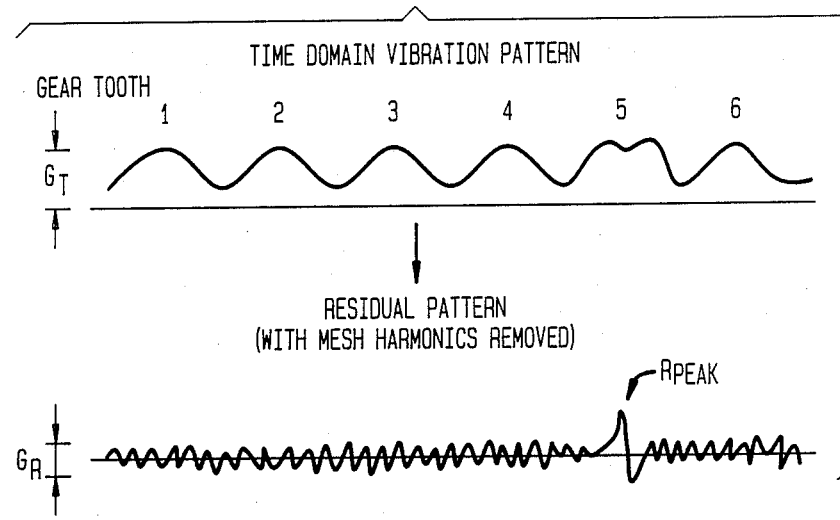
FIG. 10A illustrates the effect of the removal of mesh harmonics from the time domain vibration pattern.
Figure 10B:
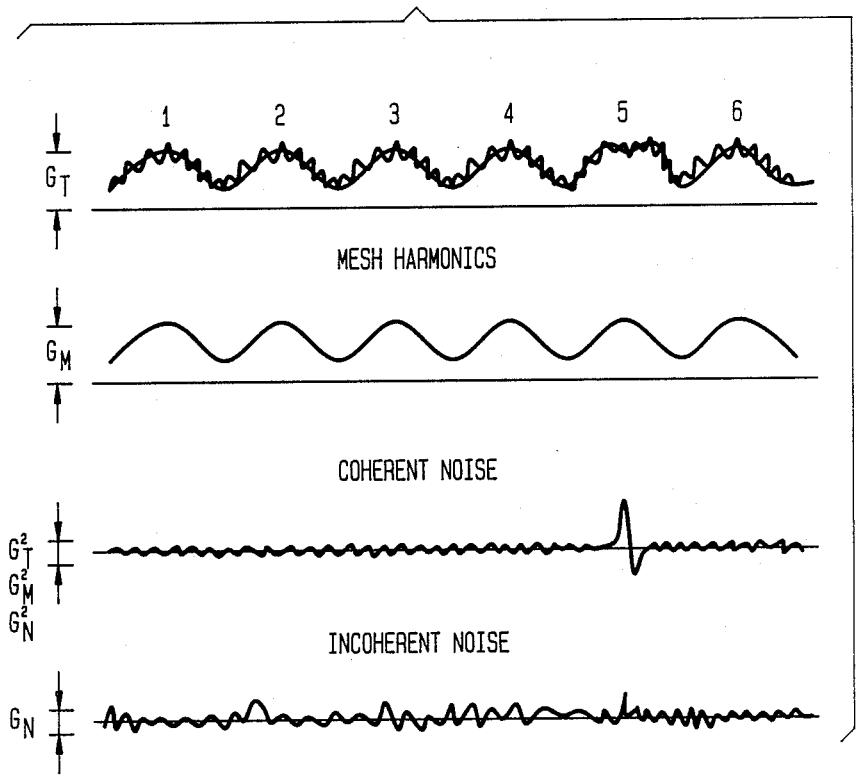
FIG. 10B illustrates that a signal is typically composed of mesh harmonics, coherent noise and incoherent noise.

The system 10 then has a choice of parallel, alternative steps. Step 6A measures defects from gear time domain averages. From the time domain average computed over one cycle of a given shaft the given "peak residual ratio" is computed as follows:

$$PRR = \frac{|R|\text{peak } \sigma R}{}$$

where $|R|$peak = peak absolute value of vibration image with DC first, second, and any interfering mesh harmonics removed $\sigma R$ = standard deviation of residual pattern σT = standard deviation of vibration image with DC, first, second, and any mesh interfering harmonics removed This measure is very effective at detecting a change in the pattern which is localized and indicative of a fault somewhere in the gear. See FIG. 10A.

Another measure which complements the foregoing measurement is the non-mesh energy ratio (NMR) corrected for incoherent noise and is good for detecting overall deterioration of vibration images due to problems like multiple tooth pitting.

This measure is computer as follows:

$$NMR = \frac{(\sigma T^2 - \sigma N^2 - \sigma m^2)}{\sigma T_2 - \sigma N^2)}$$

where
$\sigma T^2$ = variance of vibration image
$\sigma M^2$ = variance of mesh harmonics
$\sigma N^2$ = variance of incoherent noise estimate (spectral technique required for computing parameter)

All of the foregoing parameters have the DC, first and second, and any interfering mesh harmonics removed.

Figure 10C:
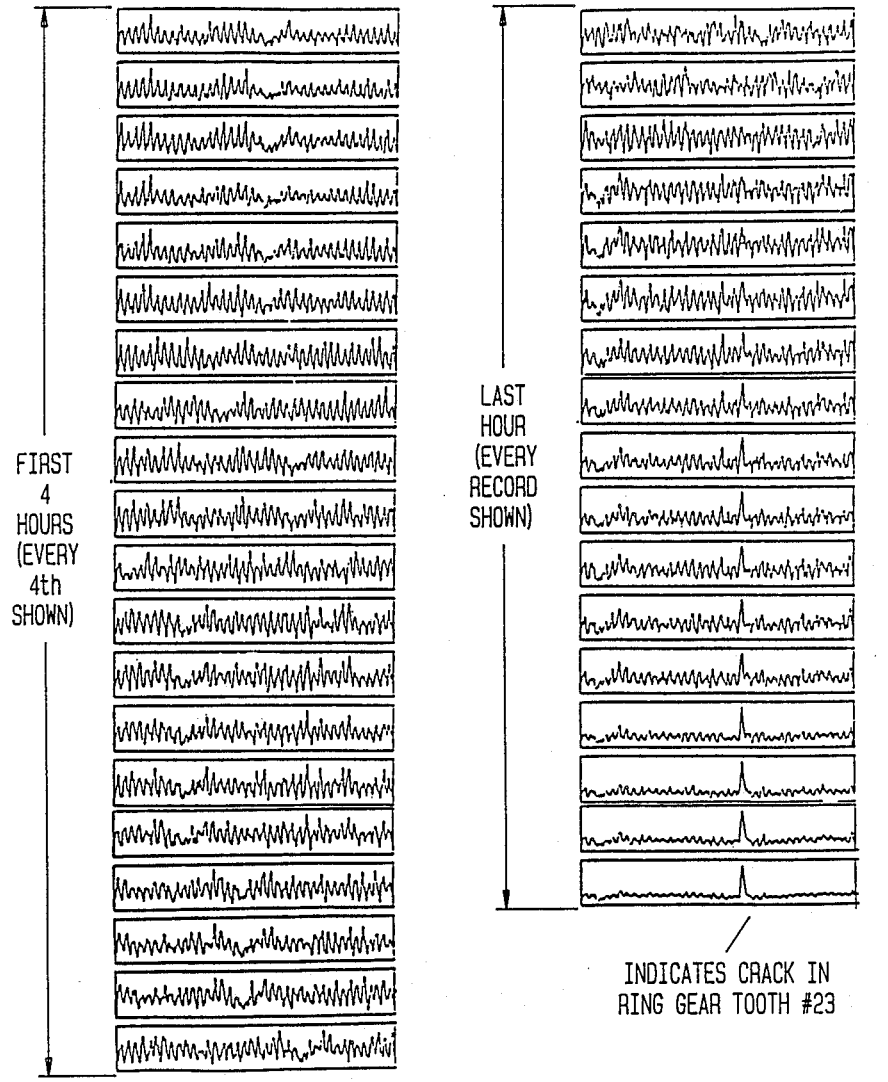
FIG. 10C illustrates the history of a gear tooth pattern showing the increase of the defect over a period of time.

Step 6B illustrated in FIG. 4A-B is an individual tooth based analysis of gear conditions. By computing one or more measures (e.g. individual amplitude) of the individual tooth vibration pattern, or the vibration pattern for an individual tooth pair (containing a hunting tooth pattern), and tracing the variation of this measure (variance, moving average based changes, transient behavior, etc.) over time, reliable indications of fault development can be obtained. FIG. 10C illustrates such a sequence of gear tooth patterns terminating in the clear anomalous behavior of one tooth which correlates with its being cracked. FIG. 10D illustrates the amplitude, in another case history, of a given tooth over time as it approaches failure. The bottom plot in FIG. 10E shows a tooth history for the adjacent tooth with respect to the figure above, which does not have dramatic changes therein.

The spectral components induced by gear modulation effects which were removed from the gear stock often contain useful information. For example, some bearing problems lead to a additive first harmonic spectral component in contrast to a multiplicative effect produced by gear runout on defective Universal joints can lead to large second harmonic components. In Step 6C of FIG. 4A-B, the amplitude of these spectral components are tracked over time.

The seventh step comprises the performance of analysis of the time histories of a given gear conditioned measured within a given system operating state. The measure of gear tooth conditions computed from the gear vibration pattern in the sixth step above are traced over time and shown in FIG. 11 (with the exception of the results of Step 6B which is already in the form of a feature history). The significant changes in such a plot are automatically detected by computer 32 and an alert is sounded through the pull up circuit 50 and alarm illustrated in FIG. 2A. According to FIG. 11, the beginning of crack generation appears early in the test giving the operator warning for test purposes, quality control inspection or preventive maintenance. Towards the end of the plot the strong rise gives warning of imminent failure. A wide variety of methods to analyze the foregoing and provide threshold warnings from the plot history can be employed. Simple amplitude thresholds that require the curve to exceed a preset level for a preset period of time can be employed to trigger appropriate warnings.

Figure 12A:
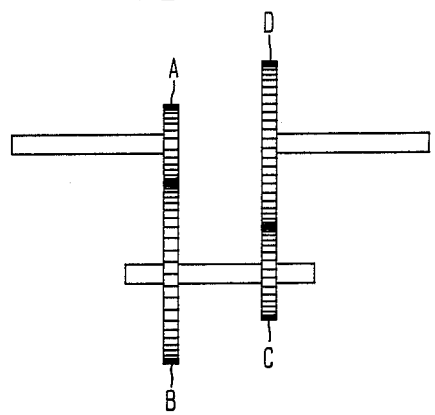
FIG. 12A illustrates another four gear/three shaft gear train.
Figure 12B:
FIG. 12B illustrates the time domain vibration pattern generated by gears A and B, and gears C and D and computed over a single rotation of gears B and C.
Figure 12C:
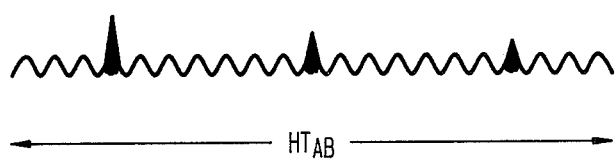
FIG. 12C illustrates the time domain vibration pattern generated by gears A and B computed over the hunting tooth cycle for A and B.
Figure 12D:
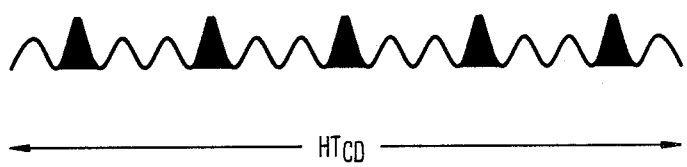
FIG. 12D illustrates the time domain vibration pattern generated by gears C and D computed over the hunting tooth cycle for C and D.

The eighth step in the process is illustrated in FIGS. 12A-12E. FIG. 12B illustrates the vibration pattern over a rotation of the BC shaft. The question is - how does one determine which gear, B or C, has the defect? According to the steps of the method illustrated in FIGS. 12C and 12D, the hunting tooth pattern for the A/B mesh is illustrated in FIG. 12C and the hunting tooth pattern for the C/D mesh is illustrated in FIGS. 12D. The variance of the tooth defect for the $HT_{AB}$ is much greater than the variance of tooth defect of $HT_{CD}$. Hence the defect lies on gear B.

Figure 12E:
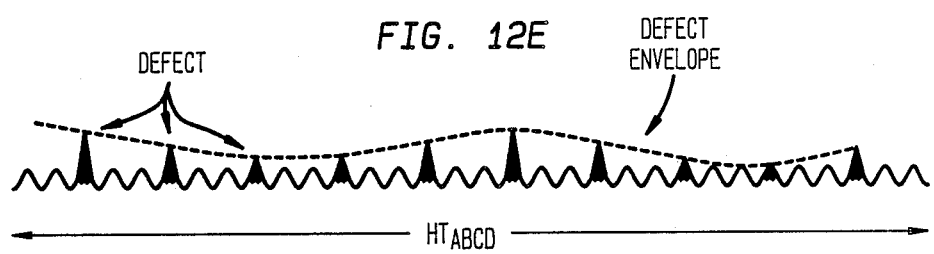
FIG. 12E illustrates a giant hunting tooth pattern including the effects of gears A, B, C and D.
Figure 12F:
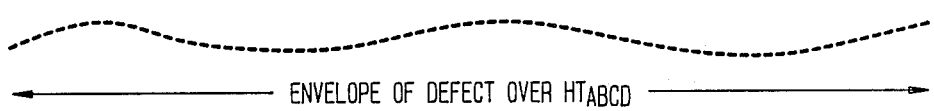
FIG. 12F illustrates the envelope of the giant hunting tooth pattern illustrated in FIG. 12D.

Alternatively, another method can be employed as illustrated in FIGS. 12E and 12F. According to the steps of the method illustrated in FIGS. 12D and 12E, a giant hunting tooth pattern $HT_{ABCD}$, i.e., the time for cycling all four gears, A, B, C, and D is employed. The envelope of the defect, which is extracted as illustrated in FIG. 12F provides the basic information. The strong component at the period of $HT_{AB}$ or $HT_{CD}$ means that the defect is on gear B or gear C respectively.

The ninth step, illustrated in FIG. 4, is to produce a status report on the different components and/or sound an alarm or otherwise shut down the monitoring system and/or perform and display the results of the analysis on monitor 34.

Figure 13:
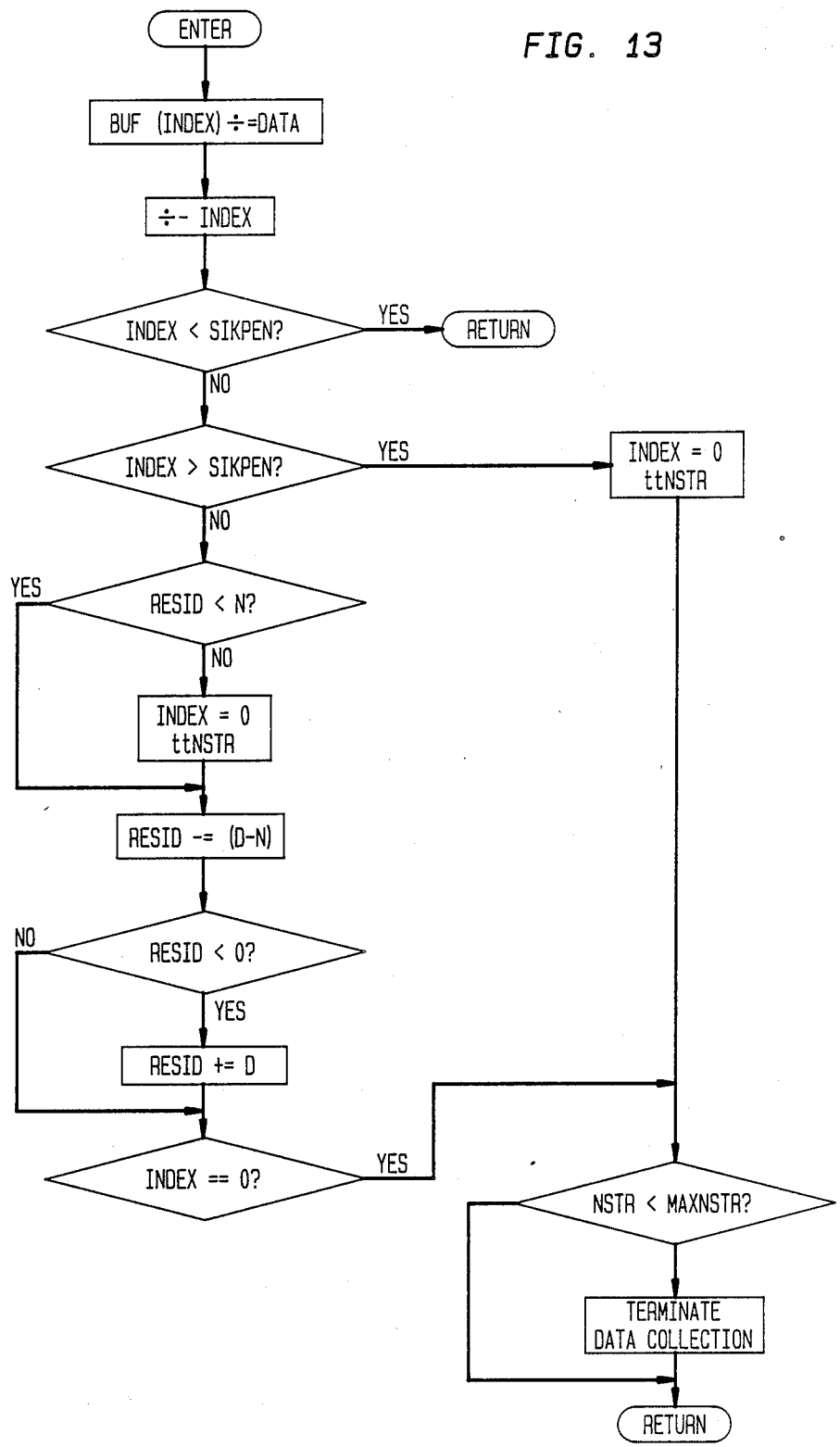
FIG. 13 represents an algorithm for stacking samples from a periodic function given a rational non-integer number of samples per period.

FIG. 13 illustrates an algorithm employed for stacking samples from a periodic function given a rational non-integer number of samples per period. The flow chart depicts an algorithm for real-time execution of a microcomputer such as 32. The algorithm is to be entered repeatedly, once per incoming data sample, until NSTK, the count of elapsed period, reaches the desired value, MAXSTK. As used in the algorithm, the following items have the following meanings.

N,D—The ratio N/D expresses fractional part of the number of samples per period, reduced to lowest terms, i.e. there are no common factors of N and D.

STKLEN—The length of the stack to be accumulated for the periodic function. STKLEN is the largest integer less then or equal to the number of samples per period.

RESID—A residual placeholder, initially zero.

BUF—A buffer of length STKLEN+1, initially all zeros, in which the stack will be accumulated.

INDEX—An index into the elements of BUF, initially zero.

NSTK—Count of elapsed periods, initially zero.

MAXSTK—Number of elapsed periods desired in the stack.

DATA—The latest sample of the incoming data stream.

A copy of the machine instruction software employed to run the system 10 from the microcomputer 32 is annexed hereto and incorporated to this disclosure in total by reference. It is possible for one of ordinary skill in the art to generate an appropriate operating program given this disclosure.

Figure 14:
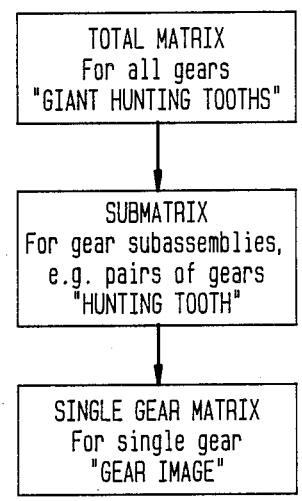
FIG. 14 is a flow diagram indicating how the matrix of collected data can be reduced and analyzed to generate different sets and subsets of information.

The total matrix of data illustrated in FIG. 14 is necessary to determine larger patterns such as the giant hunting tooth pattern. Reduced sets of data from the total matrix can be used to obtain a submatrix to detect a single hunting tooth pair of gears and that submatrix can be further reduced to a smaller single gear data matrix to produce a single gear image.

The advantages of the foregoing system 10 include the following.

1. The system 10 produces a vibration based image of individual gear teeth in operating machinery which reveal important aspects of their conditions.

2. The system 10 provides an automatic measure of the quality (e.g. signal to noise ratio) of the gear image to aid in interpretation.

3. The system 10 detects, quantifies, classifies, automatically analyzes gear images evolving over time and can also forecast gear problems, and display any of this information to the operator.

4. The system 10 utilizes novel methods to detect, evaluate, and eliminate interfering spectral contributions.

5. The system 10 utilizes novel deconvolution techniques to remove leakage of images of adjacent gears which are normally present in standard synchronous gear imaging.

6. The system 10 can produce a hunting tooth gear image in order to interpret gear tooth status. This technique is especially effective for interpreting tooth-to-tooth specific interaction.

7. The system 10 utilizes selectable frequency bands, shaft synchronized coherent processing, sensors attachable outside the equipment and automatically compensates for variable operating speeds (i.e. it is shaft synchronized).

8. In the system 10 only, a single shaft of a multiple shaft gear train need be synchronized for all of the gear images to be produced.

9. The system 10 can perform a stack of data where the number of samples per stack period is an irrational number (not an integer).

10. The system 10 includes a means and method to detect which gear of a multiple gear shaft has the defect and further, it includes the means to automatically separate mesh patterns.

11. The system 10 permits in-process operator controlled analysis through Discrete Fourier Transform, FFT, specialized filtering and references to other data.

12. Analog preprocessing of the signal is automatically set up through the use of a computer-controlled analog board with a variety of programmable functions including shaft synchronized A/D and a D/A for self-calibration and system checks.

13. The system 10 can be implemented using an off-the-shelf high speed microcomputer.

14. The system 10 produces data regarding the condition of other moving interactions including U-joints, pinion bearings, and ring bearings when applied to the testing of axles.

15. The system 10 utilizes pulse multiplier boards to enable operation from shaft encoders which give too few or too many pulses per shaft turn.

16. The system 10 provides other functions in that it detects, quantifies, and classifies quality of machinery based on mesh harmonic amplitude vs. RPM measurements. This feature is important for the testing of quality control of transmissions and the like and is currently not believed to be performed because of the cost required for the computer analysis. The present system 10 allows all such information to be obtained through the use of relatively inexpensive PC-AT type microcomputers 32 and an appropriate analog preprocessing board which includes a low pass tracking filter.

While the invention has been described with reference to the preferred embodiment thereof, it will be appreciated by those of ordinary skill in the art that various modifications and changes can be made to the parts and steps which comprise the invention without departing from the spirit and scope thereof as a whole.

We claim:

1. A method for analyzing a gear system having at least two inter-meshing gears, comprising the steps of:

sensing data signals produced by tooth-to-tooth contact in said gear system as said gears revolve, wherein at least some of said data is sensed by shaft encoders and wherein said data signals include signals from at least two top-dead-center pickup means for determining the unique angular orientation of each gear of said gear system;

acquiring additional data from said system, including the number of teeth on each gear, the gear system configuration, and the given machine operating state;

identifying from the combined data, which includes the additional data and the data signals, the relative angular orientation of the gears in said system and the data generated at said orientation; and analyzing the combined data to compute gear system vibrational characteristics.

2. The method of claim 1 further comprising the step of:

logically combining the signals from said at least two of said top-dead-center pickup means in order to insure that data signals acquisition is initiated at a fixed cycle position of the gears in said gear system.

3. A method for detecting gear defects in a system having at least four gears comprising the steps of:

collecting signal data relating to the interaction of a first pair of gears including a first gear and a second gear;

collecting signal data from a second pair of gears which includes a third gear which interacts with a fourth gear, said third and said first gear being located on a common shaft;

combining the signals collected from said first, second, third and fourth gears together to form a giant hunting tooth pattern; and, detecting the envelope of said giant hunting tooth pattern, wherein the period of the peaks of the envelope which corresponds to the hunting tooth of either pair indicates on which pair of gears a defect is likely to be found.

4. A method of analyzing a vibrational signal generated by the inter-meshing of at least two gears, said analysis comprising the steps of:

sensing said vibrational signal at least long enough for each tooth of said gears to mate once before repeating;

stacking at least two of said signals so that identical tooth-to-tooth matings are superimposed on each other; and determining which tooth-to-tooth interactions have anomalous patterns, wherein the tooth-to-tooth interactions which have anomalous patterns determined above are likely to include a gear having a defect therein.

5. The method of claim 4 further comprises the step of:

detecting the envelope of said stacked signals to identify the peak thereof which are likely to indicate teeth containing defects.

6. A system for analyzing a vibrational signal generated by at least two inter-meshing gears, said system comprising:
- a vibrational signal pickup mountable on an object;
- an interface connected to said pickup;
- an analog signal processor means connected to said interface for conditioning and converting said signal to a digital signal;
- a computer means connected to said analog signal processor means for recording the digital signal over at least one hunting tooth period of said gears and stacking at least two of said signals so that tooth-by-tooth interactions are superimposed on each tooth; and,
- an output means for reporting the results of the operations performed by said computer means.

7. The system of claim 6 further comprising of:
- a shaft encoder connected to said rotating object to produce an output signal each time said object rotates; and
- a pulse multiplier means to change the number of pulses produced by said shaft encoder to a rate optimally compatible with said computer means.

8. The system of claim 6 wherein said output means comprises a CRT monitor.

9. The system of claim 8 wherein said output means includes an alarm to indicate when said signal analyzed by said computer means exceeds a pre-determined threshold.

10. A method of detecting the location of a defect in a gear system of at least two gears, said method comprising the steps of:
- generating a series of hunting tooth patterns of the tooth-by-tooth interactions of at least two gears; and,
- comparing the hunting tooth patterns generated over time against each other to locate local gear defects,
- wherein said hunting tooth patterns are as long as it takes for each tooth-by-tooth interaction to repeat itself.

11. A method for analyzing a vibrational signal generated by at least two inter-meshing gears, comprising the steps of:
- detecting said vibrational signal;
- high frequency band pass filtering said vibrational signal;
- detecting the envelope of said high frequency band pass filtered signal to produce a signal representative of the low frequency components of said vibrational signal; and,
- stacking at least two of said envelopes so that vibrations of the same tooth are superimposed on each other,
- wherein the stacking of said envelopes produces an indication of gear tooth anomalies.

* * * * *